US010420935B2

(12) United States Patent
Illegems et al.

(10) Patent No.: US 10,420,935 B2
(45) Date of Patent: Sep. 24, 2019

(54) CONTROLLER FOR NERVE STIMULATION CIRCUIT AND ASSOCIATED SYSTEMS AND METHODS

(71) Applicant: Nevro Corp., Redwood City, CA (US)

(72) Inventors: Paul Illegems, Redwood City, CA (US); Jon Parker, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 15/381,769

(22) Filed: Dec. 16, 2016

(65) Prior Publication Data
US 2017/0197079 A1    Jul. 13, 2017

Related U.S. Application Data

(60) Provisional application No. 62/273,810, filed on Dec. 31, 2015, provisional application No. 62/287,875, filed on Jan. 27, 2016.

(51) Int. Cl.
*A61N 1/32* (2006.01)
*A61N 1/36* (2006.01)
(Continued)

(52) U.S. Cl.
CPC ....... *A61N 1/36021* (2013.01); *A61N 1/0551* (2013.01); *A61N 1/32* (2013.01);
(Continued)

(58) Field of Classification Search
CPC .............. A61N 1/36071; A61N 1/3787; A61N 1/0551; A61N 1/08
See application file for complete search history.

(56) References Cited

U.S. PATENT DOCUMENTS 3,871,382 A    3/1975 Mann
4,071,032 A    1/1978 Schulman
(Continued)

FOREIGN PATENT DOCUMENTS

EP    1610437    12/2005
EP    2243510    10/2010
(Continued)

OTHER PUBLICATIONS

International Search Report and Written Opinion for International Patent Application No. PCT/US16/67217, Applicant; Nevro Corp., dated Apr. 21, 2017, 18 pages.
(Continued)

*Primary Examiner* — Michael J D Abreu
(74) *Attorney, Agent, or Firm* — Perkins Coie LLP (57) ABSTRACT

Disclosed is a voltage monitoring circuit for use in detecting if a voltage supplied to current-generating circuit is sufficient to allow the current-generating circuit to produce a desired current. In one embodiment the circuit is designed for use in an implantable device that is configured to deliver therapeutic pulses to a patient. The voltage monitoring circuit is configured to produce a signal if a supplied voltage is insufficient to allow a current-generating circuit to deliver a requested current to a set of electrodes. In one embodiment, the voltage monitoring circuit detects a change in a difference between the voltage at a node in the current-generating circuit and the supplied voltage.

9 Claims, 5 Drawing Sheets

(51) Int. Cl.
  *G05F 3/26* (2006.01)
  *A61N 1/05* (2006.01)
  *A61N 1/372* (2006.01)
(52) U.S. Cl.
  CPC ....... *A61N 1/3605* (2013.01); *A61N 1/36067* (2013.01); *A61N 1/36071* (2013.01); *A61N 1/37211* (2013.01); *G05F 3/262* (2013.01)

(56) References Cited

U.S. PATENT DOCUMENTS

| | | |
|---|---|---|
| 4,082,097 A | 4/1978 | Mann et al. |
| D250,719 S | 1/1979 | Jacobson et al. |
| 4,197,850 A | 4/1980 | Schulman et al. |
| 4,230,121 A | 10/1980 | Stanton |
| 4,441,498 A | 4/1984 | Nordling |
| D280,930 S | 10/1985 | Speicher et al. |
| 4,632,117 A | 12/1986 | James |
| 4,890,616 A | 1/1990 | Pinckaers |
| 5,065,083 A | 11/1991 | Owens |
| 5,144,946 A | 9/1992 | Weinberg et al. |
| D337,820 S | 7/1993 | Hooper et al. |
| 5,279,292 A | 1/1994 | Baumann et al. |
| D343,901 S | 2/1994 | Anderson |
| 5,733,313 A | 3/1998 | Barreras, Sr. et al. |
| 5,769,877 A | 6/1998 | Barreras, Sr. |
| 5,807,397 A | 9/1998 | Barreras |
| 5,928,272 A | 7/1999 | Adkins et al. |
| 5,954,758 A | 9/1999 | Peckham et al. |
| 6,026,328 A | 2/2000 | Peckham et al. |
| 6,076,018 A | 6/2000 | Sturman et al. |
| 6,115,634 A | 9/2000 | Donders et al. |
| 6,167,303 A | 12/2000 | Thompson |
| 6,185,452 B1 | 2/2001 | Schulman et al. |
| 6,185,454 B1 | 2/2001 | Thompson |
| 6,223,080 B1 | 4/2001 | Thompson |
| 6,236,888 B1 | 5/2001 | Thompson |
| 6,324,426 B1 | 11/2001 | Thompson |
| 6,434,425 B1 | 8/2002 | Thompson |
| 6,453,198 B1 | 9/2002 | Torgerson et al. |
| 6,472,991 B1 | 10/2002 | Schulman et al. |
| 6,496,729 B2 | 12/2002 | Thompson |
| 6,553,263 B1 | 4/2003 | Meadows et al. |
| D478,990 S | 8/2003 | Kroll |
| 6,650,943 B1 | 11/2003 | Whitehurst et al. |
| 6,712,772 B2 | 3/2004 | Cohen et al. |
| 6,757,561 B2 | 6/2004 | Rubin et al. |
| 6,871,099 B1 | 3/2005 | Whitehurst et al. |
| 7,027,860 B2 | 4/2006 | Bruninga et al. |
| 7,054,689 B1 | 5/2006 | Whitehurst et al. |
| D523,144 S | 6/2006 | Wenger et al. |
| 7,120,499 B2 | 10/2006 | Thrope et al. |
| 7,127,288 B2 | 10/2006 | Sturman et al. |
| 7,142,923 B2 | 11/2006 | North et al. |
| 7,167,756 B1 | 1/2007 | Torgerson et al. |
| 7,177,703 B2 | 2/2007 | Boveja et al. |
| 7,184,836 B1 | 2/2007 | Meadows et al. |
| 7,209,792 B1 | 4/2007 | Parramon et al. |
| 7,254,449 B2 | 8/2007 | Karunasiri |
| 7,263,405 B2 | 8/2007 | Boveja et al. |
| D559,987 S | 1/2008 | Strother et al. |
| 7,330,762 B2 | 2/2008 | Boveja et al. |
| 7,337,010 B2 | 2/2008 | Howard et al. |
| 7,437,193 B2 | 10/2008 | Parramon et al. |
| 7,444,184 B2 | 10/2008 | Boveja et al. |
| 7,489,968 B1 | 2/2009 | Alexander |
| 7,496,404 B2 | 2/2009 | Meadows et al. |
| 7,571,002 B2 | 8/2009 | Thrope et al. |
| 7,606,622 B2 | 10/2009 | Reeve |
| 7,616,990 B2 | 11/2009 | Chavan et al. |
| 7,620,454 B2 | 11/2009 | Dinsmoor et al. |
| 7,636,602 B2 | 12/2009 | Baru Fassio et al. |
| 7,641,992 B2 | 1/2010 | Howard et al. |
| 7,650,191 B1 | 1/2010 | Lim et al. |
| D610,261 S | 2/2010 | Strother et al. |
| 7,682,745 B2 | 3/2010 | Howard et al. |
| 7,697,984 B2 | 4/2010 | Hill et al. |
| 7,769,442 B2 | 8/2010 | Shafer |
| 7,769,462 B2 | 8/2010 | Meadows et al. |
| 7,801,601 B2 | 9/2010 | Maschino et al. |
| 7,801,615 B2 | 9/2010 | Meadows et al. |
| 7,818,068 B2 | 10/2010 | Meadows et al. |
| 7,848,812 B2 | 12/2010 | Crowley |
| 7,865,245 B2 | 1/2011 | Torgerson et al. |
| 7,879,495 B2 | 2/2011 | Howard et al. |
| 7,894,905 B2 | 2/2011 | Pless |
| 7,916,013 B2 | 3/2011 | Stevenson |
| 7,941,220 B2 | 5/2011 | Tobacman |
| 8,128,600 B2 | 3/2012 | Gill |
| D663,035 S | 7/2012 | Smith |
| D665,086 S | 8/2012 | Smith |
| D665,087 S | 8/2012 | Smith |
| 8,355,797 B2 | 1/2013 | Caparso et al. |
| 8,571,679 B2 | 10/2013 | Parramon et al. |
| 8,965,514 B2 | 2/2015 | Bikson et al. |
| 9,061,152 B2 * | 6/2015 | Shi ..................... A61N 1/36071 |
| 9,192,769 B2 | 11/2015 | Donofrio et al. |
| 9,227,076 B2 | 1/2016 | Sharma et al. |
| 9,409,020 B2 | 8/2016 | Parker |
| 9,884,198 B2 | 2/2018 | Parker et al. |
| 2002/0107554 A1 | 8/2002 | Biggs et al. |
| 2002/0193844 A1 | 12/2002 | Michelson et al. |
| 2003/0114899 A1 | 6/2003 | Woods et al. |
| 2003/0135241 A1 | 7/2003 | Leonard et al. |
| 2003/0191504 A1 | 10/2003 | Meadows et al. |
| 2003/0195581 A1 | 10/2003 | Meadows et al. |
| 2003/0204222 A1 | 10/2003 | Leinders et al. |
| 2003/0208244 A1 * | 11/2003 | Stein .................. A61N 1/37241 607/48 |
| 2004/0098060 A1 | 5/2004 | Ternes |
| 2004/0215287 A1 | 10/2004 | Swoyer et al. |
| 2005/0131467 A1 | 6/2005 | Boveja |
| 2005/0131486 A1 | 6/2005 | Boveja et al. |
| 2005/0131487 A1 | 6/2005 | Boveja et al. |
| 2005/0137644 A1 | 6/2005 | Boveja et al. |
| 2005/0143787 A1 | 6/2005 | Boveja et al. |
| 2005/0149146 A1 | 7/2005 | Boveja et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0197678 A1 | 9/2005 | Boveja et al. |
| 2005/0203583 A1 | 9/2005 | Twetan |
| 2005/0203584 A1 | 9/2005 | Twetan et al. |
| 2005/0216070 A1 | 9/2005 | Boveja et al. |
| 2005/0266301 A1 | 12/2005 | Smith et al. |
| 2005/0267546 A1 | 12/2005 | Parramon et al. |
| 2007/0060955 A1 | 3/2007 | Strother et al. |
| 2007/0060968 A1 | 3/2007 | Strother et al. |
| 2007/0060980 A1 | 3/2007 | Strother et al. |
| 2007/0111587 A1 | 5/2007 | Ries et al. |
| 2007/0213783 A1 | 9/2007 | Pless |
| 2007/0265489 A1 | 11/2007 | Fowler et al. |
| 2007/0270916 A1 | 11/2007 | Fischell et al. |
| 2008/0039904 A1 | 2/2008 | Bulkes et al. |
| 2008/0058901 A1 | 3/2008 | Ternes et al. |
| 2008/0065182 A1 | 3/2008 | Strother et al. |
| 2008/0077184 A1 | 3/2008 | Denker et al. |
| 2008/0097554 A1 | 4/2008 | Payne et al. |
| 2008/0125833 A1 | 5/2008 | Bradley et al. |
| 2008/0129225 A1 | 6/2008 | Yamamoto et al. |
| 2008/0132926 A1 | 6/2008 | Eichmann et al. |
| 2008/0156333 A1 | 7/2008 | Galpern et al. |
| 2008/0216846 A1 | 9/2008 | Levin |
| 2008/0255631 A1 | 10/2008 | Sjostedt et al. |
| 2008/0262563 A1 | 10/2008 | Sjostedt |
| 2008/0294219 A1 | 11/2008 | Osypka et al. |
| 2009/0012576 A1 | 1/2009 | Erbstoeszer et al. |
| 2009/0017700 A1 | 1/2009 | Zart et al. |
| 2009/0018600 A1 | 1/2009 | Deininger et al. |
| 2009/0018607 A1 | 1/2009 | Crowley et al. |
| 2009/0132010 A1 | 5/2009 | Kronberg |
| 2009/0157142 A1 | 6/2009 | Cauller |
| 2009/0204119 A1 | 8/2009 | Bleich et al. |

(56) References Cited

U.S. PATENT DOCUMENTS

| | | |
|---|---|---|
| 2009/0204173 A1 | 8/2009 | Fang et al. |
| 2009/0210029 A1 | 8/2009 | Tsui |
| 2009/0228074 A1 | 9/2009 | Edgell et al. |
| 2009/0248094 A1 | 10/2009 | McDonald |
| 2009/0248118 A1 | 10/2009 | Bradley et al. |
| 2009/0270948 A1 | 10/2009 | Nghiem et al. |
| 2009/0281596 A1 | 11/2009 | King et al. |
| 2010/0004654 A1 | 1/2010 | Schmitz et al. |
| 2010/0010567 A1 | 1/2010 | Deem et al. |
| 2010/0038132 A1 | 2/2010 | Kinney et al. |
| 2010/0049275 A1 | 2/2010 | Chavan et al. |
| 2010/0094115 A1 | 4/2010 | Pond, Jr. et al. |
| 2010/0094231 A1 | 4/2010 | Bleich et al. |
| 2010/0106223 A1 | 4/2010 | Grevious et al. |
| 2010/0137943 A1 | 6/2010 | Zhu |
| 2010/0137944 A1 | 6/2010 | Zhu |
| 2010/0144281 A1 | 6/2010 | Kim et al. |
| 2010/0144283 A1 | 6/2010 | Curcio et al. |
| 2010/0168818 A1 | 7/2010 | Barror et al. |
| 2010/0233896 A1 | 9/2010 | Dilmaghanian |
| 2010/0274314 A1 | 10/2010 | Alataris et al. |
| 2010/0274317 A1 | 10/2010 | Parker et al. |
| 2010/0305631 A1 | 12/2010 | Bradley et al. |
| 2010/0305663 A1 | 12/2010 | Aghassian |
| 2010/0324570 A1 | 12/2010 | Rooney et al. |
| 2011/0054583 A1 | 3/2011 | Litt et al. |
| 2011/0071593 A1 | 3/2011 | Parker et al. |
| 2011/0112601 A1 | 5/2011 | Meadows et al. |
| 2011/0112609 A1 | 5/2011 | Peterson |
| 2011/0144468 A1 | 6/2011 | Boggs et al. |
| 2011/0224710 A1 | 9/2011 | Bleich |
| 2012/0095744 A1 | 4/2012 | Rahman |
| 2012/0315798 A1 | 12/2012 | Poon et al. |
| 2013/0035740 A1 | 2/2013 | Sharma |
| 2013/0066399 A1 | 3/2013 | Min |
| 2013/0066411 A1 | 3/2013 | Thacker et al. |
| 2013/0238048 A1 | 9/2013 | Almendinger et al. |
| 2014/0277268 A1 | 9/2014 | Lee |
| 2016/0114171 A1 | 4/2016 | Parker |
| 2016/0256696 A1 | 9/2016 | Sharma |
| 2017/0036023 A1 | 2/2017 | Parker |

FOREIGN PATENT DOCUMENTS

| | | |
|---|---|---|
| JP | 2002090196 | 3/2002 |
| WO | WO-2008121110 | 10/2008 |
| WO | WO-2011094074 A1 | 8/2011 |
| WO | WO-2012054234 | 4/2012 |

OTHER PUBLICATIONS

Gainer et al., "Use of the Peripheral Nerve Stimulator and Standard, Unsheathed Needles in Performing Regional Nerve Blocks," CRNA: The Clinical Forum for Nurse Anesthetists, vol. 3, No. 4, Nov. 1992, 4 pages.

Hoist et al., "Nervous Control of Pancreatic exocrine secretion in pigs," Acta, Physiol. Scan 1979, 105, 19 pages.

Huxely et al., "Excitation and Conduction in Nerve: Quantitative Analysis," Science, Sep. 11, 1964; 145: 1154-9.

Klein, "Continuous Peripheral Nerve Blocks," Anesthesiology, vol. 103, No. 5, Nov. 2005, 3 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Linderoth et al., "Mechanisms of Spinal Cord Stimulation in Painful Syndromes: Role of Animal Models," Pain Medicine, vol. 7, No. S1, 2006, 13 pages.

Mediati, R.D. "Mechanisms of Spinal Cord Stimulation," Florence, Oct. 2, 2002, 31 pages.

North et al., "Spinal Cord Stimulation for Axial Low Back Pain," SPINE, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

Paterson CA et al., "Determinants of Occurrence and Volume of Transpyloric Flow During Gastric Emptying of Liquids in Dogs: Importance of Vagal Input," Dig Dis Sci, 2000, 45: 1509-1516.

Vadalouca et al., "Therapeutic Management of Chronic Neuropathic Pain: An Examination of Pharmacologic Treatment," Annals New York Academy of Sciences, 2006, pp. 164-186.

Extended European Search Report for European Patent Application No. 16882338.3, Applicant: Nevro Corporation, dated Jun. 18, 2019, 11 pages.

\* cited by examiner

CONTROLLER FOR NERVE STIMULATION CIRCUIT AND ASSOCIATED SYSTEMS AND METHODS

TECHNICAL FIELD

The disclosed technology relates generally to implantable nerve stimulation circuits and in particular, to circuits for adjusting battery power consumption in an implantable nerve stimulation circuit and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and may be implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS for the treatment of pain, the signal generator applies electrical pulses to the spinal cord via the electrodes. In conventional SCS, "low frequency" electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

As with any implantable device, battery life is an important design concern. If the supply voltage that is applied to the current-generating circuitry is too low, then the circuits will not operate as desired. On the other hand, if the supply voltage applied to the circuitry is too high, then battery power is being unnecessarily wasted and the battery will have to be re-charged sooner rather than later. The amount of supplied voltage that is above the level required to operate the circuitry is generally referred to as the current source supply voltage "headroom."

As will be explained in detail below, the disclosed technology relates to circuitry for detecting if a supply voltage is insufficient to allow the current-generating circuitry in an implantable nerve stimulation device to operate properly.

DETAILED DESCRIPTION

The disclosed technology relates generally to systems and methods for managing battery power in an implantable medical device that delivers therapeutic currents to a patient. In one embodiment, the disclosed technology determines when a voltage supplied to a current-generating circuit is not sufficient to allow the current generating circuit to supply a requested current to one or more electrodes. In one embodiment, a processor is programmed to control the voltage supplied to the current-generating circuit to minimize unnecessary power drain from a battery.

General aspects of the environments in which the disclosed technology operates are described below under Heading 1.0 ("Overview") with reference to FIG. 1. Particular embodiments of the technology are described further under Heading 2.0 ("Representative Embodiments") with reference to FIGS. 2-5. Additional embodiments are described under Heading 3.0 ("Additional Embodiments").

1.0 Overview

Figure 1:
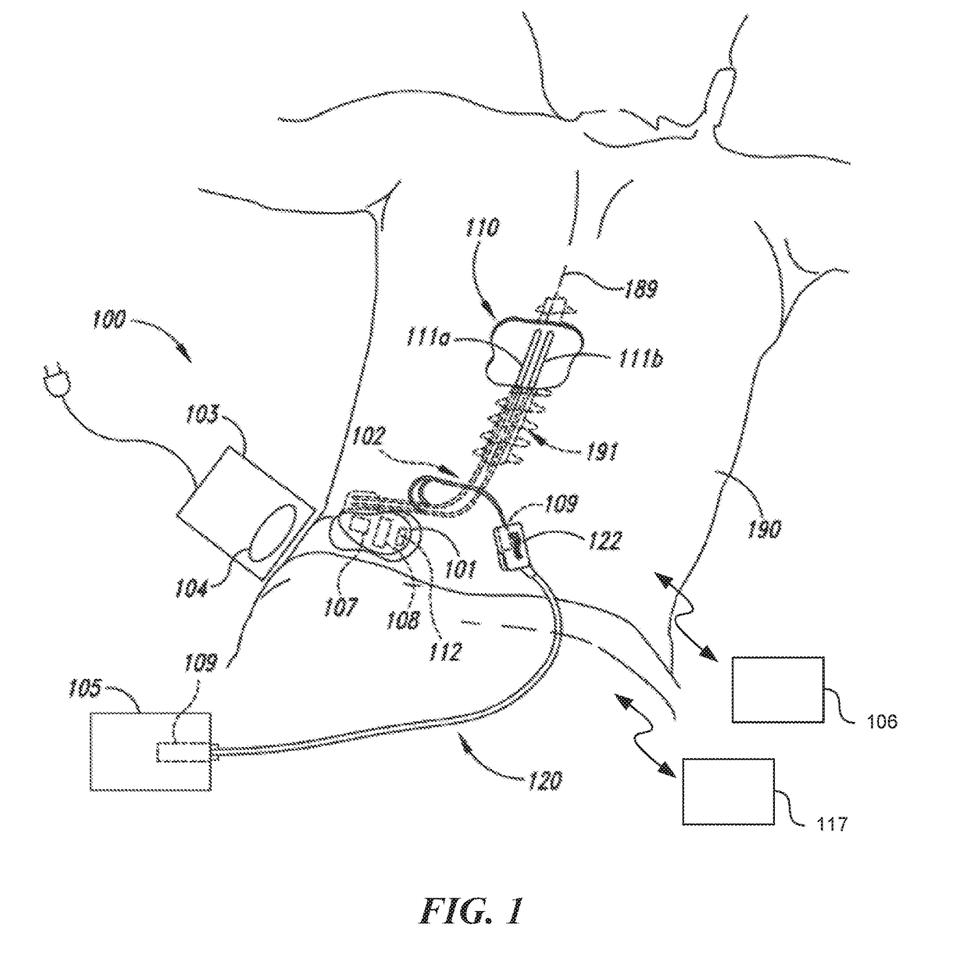
FIG. 1 is a partially schematic illustration of an implantable spinal cord stimulation system positioned at a patient's spine to deliver therapeutic signals in accordance with several embodiments of the present technology.

FIG. 1 schematically illustrates a representative patient therapy system 100 for providing relief from chronic pain and/or other conditions, arranged relative to the general anatomy of a patient's spinal column 191. The system 100 can include a signal generator 101 (e.g., an implanted or implantable pulse generator or IPG), which may be implanted subcutaneously within a patient 190 and coupled to one or more signal delivery elements or devices 110. The signal delivery elements or devices 110 may be implanted within the patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 211 (identified individually as a first lead 111*a* and a second lead 111*b*). As used herein, the terms signal delivery device, lead, and/or lead body include any of a number of suitable substrates and/or support members that carry electrodes/devices for providing therapy signals to the patient 190. For example, the lead or leads 111 can include one or more electrodes or electrical contacts that direct electrical signals into the patient's tissue, e.g., to provide for therapeutic relief. In other embodiments, the signal delivery elements 110 can include structures other than a lead body (e.g., a paddle) that also direct electrical signals and/or other types of signals to the patient 190.

In a representative embodiment, one signal delivery device may be implanted on one side of the spinal cord midline 189, and a second signal delivery device may be implanted on the other side of the spinal cord midline 189. For example, the first and second leads 111*a*, 111*b* shown in FIG. 1 may be positioned just off the spinal cord midline 189 (e.g., about 1 mm offset) in opposing lateral directions so that the two leads 111a, 111b are spaced apart from each other by about 2 mm. In particular embodiments, the leads 111 may be implanted at a vertebral level ranging from, for example, about T8 to about T12. In other embodiments, one or more signal delivery devices can be implanted at other vertebral levels, e.g., as disclosed in U.S. Patent Application Publication No. 2013/0066411, which is incorporated herein by reference in its entirety.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described herein; e.g., the methods, processes, and/or sub-processes described with reference to FIGS. 2-5 below. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1, or in multiple housings.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1 for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 210 can obtain power to generate the therapy signals from an external power source 103. In one embodiment, for example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 201, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure. Further aspects of these and other expected beneficial results are detailed in U.S. Patent Application Publication No. 2013/0066411 (previously incorporated by reference as Appendix A), and U.S. Patent Application Publication Nos. 2010/0274314; 2009/0204173; and 2010/0274317, each of which is incorporated herein by reference in its entirety.

2.0 Representative Embodiments

Figure 2:
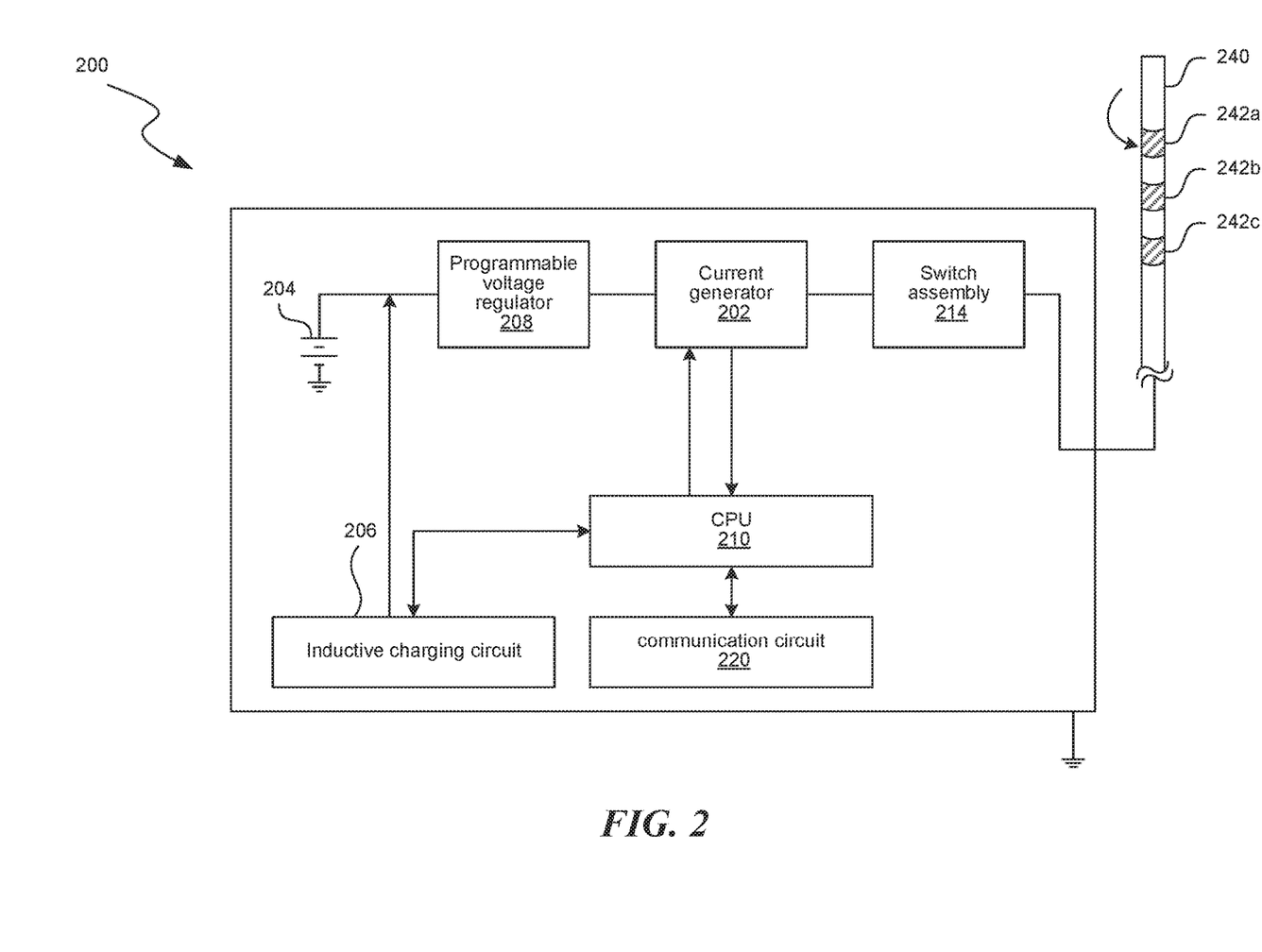
FIG. 2 is a simplified block diagram of an implantable therapeutic device in accordance with a disclosed embodiment of the present technology.

FIG. 2 shows a simplified block diagram of an implantable therapeutic device 200 configured in accordance with an embodiment of the disclosed technology. The implantable device includes a current-generating circuit 202 (labelled current generator) that produces therapeutic currents for one or more electrode leads 240 or other signal delivery device (s). The therapeutic device further includes a rechargeable battery 204 and an inductive charging circuit 206 that is used to recharge the battery from an external charger 103. Alternatively, the battery 204 may be a single-use battery that must be periodically replaced. The therapeutic device also includes a logic circuit or processor (CPU) 210 (e.g., a microprocessor, a microcontroller, digital signal processor FPGA, ASIC or the like). Voltage from the battery 204 is supplied to a programmable voltage regulator 208 that produces a variable supply voltage to the current-generating circuit 202 under the control of the processor 210. In one embodiment, the battery 204 is a lithium ion battery that produces a voltage of approximately 3.2 volts when fully charged. The programmable voltage regulator 208 can increase this voltage to a higher level (e.g., 4-20 volts) or can decrease the voltage, e.g. down to approximately 2.0 volts or lower.

In one embodiment, the processor 210 is programmed to send signals to the programmable voltage regulator 208 to adjust the voltage supplied to the current generating circuit 202 so that the current generating circuit 202 can supply a requested current to the electrodes on the lead(s) 240 but not supply a voltage that is so high that battery power is wasted.

A programmable switch assembly 214 in the implantable device 200 is used to configure connections to the electrodes 242 on the leads 240 in order to control how the requested current is delivered to the patient. The switch assembly 214 is controlled by the processor 210 so that currents can be delivered between any of the electrodes 242 on the lead (e.g., between one or more "anode" contacts and one or more cathode contacts to operate the device in a bi-polar or other multi-polar manner). Alternatively, the programmable switch assembly 214 can configure the connections to the contacts so that currents flow between one or more of the contacts 242 and a remote common electrode or contact (such as the case of the implantable device) in order to operate the contacts 242 in a uni-polar manner.

In one embodiment, the implantable device 200 includes a wireless communication circuit 220 that transmits and receives signals from an external programmer 106, 117 shown in FIG. 1, in order to control the therapies that are delivered to the patient, to supply a doctor or technician with information about the operation of the device, to update the operating program or parameters of the device and for other uses.

As discussed above, it is desirable that the voltage supplied by the programmable voltage regulator 208 is sufficient to allow the current-generating circuit 202 to generate the requested currents for delivery to the contacts. On the other hand, if the voltage supplied to the current-generating circuit is more than the voltage needed, battery power is wasted and battery power will be depleted unnecessarily.

Figure 3:
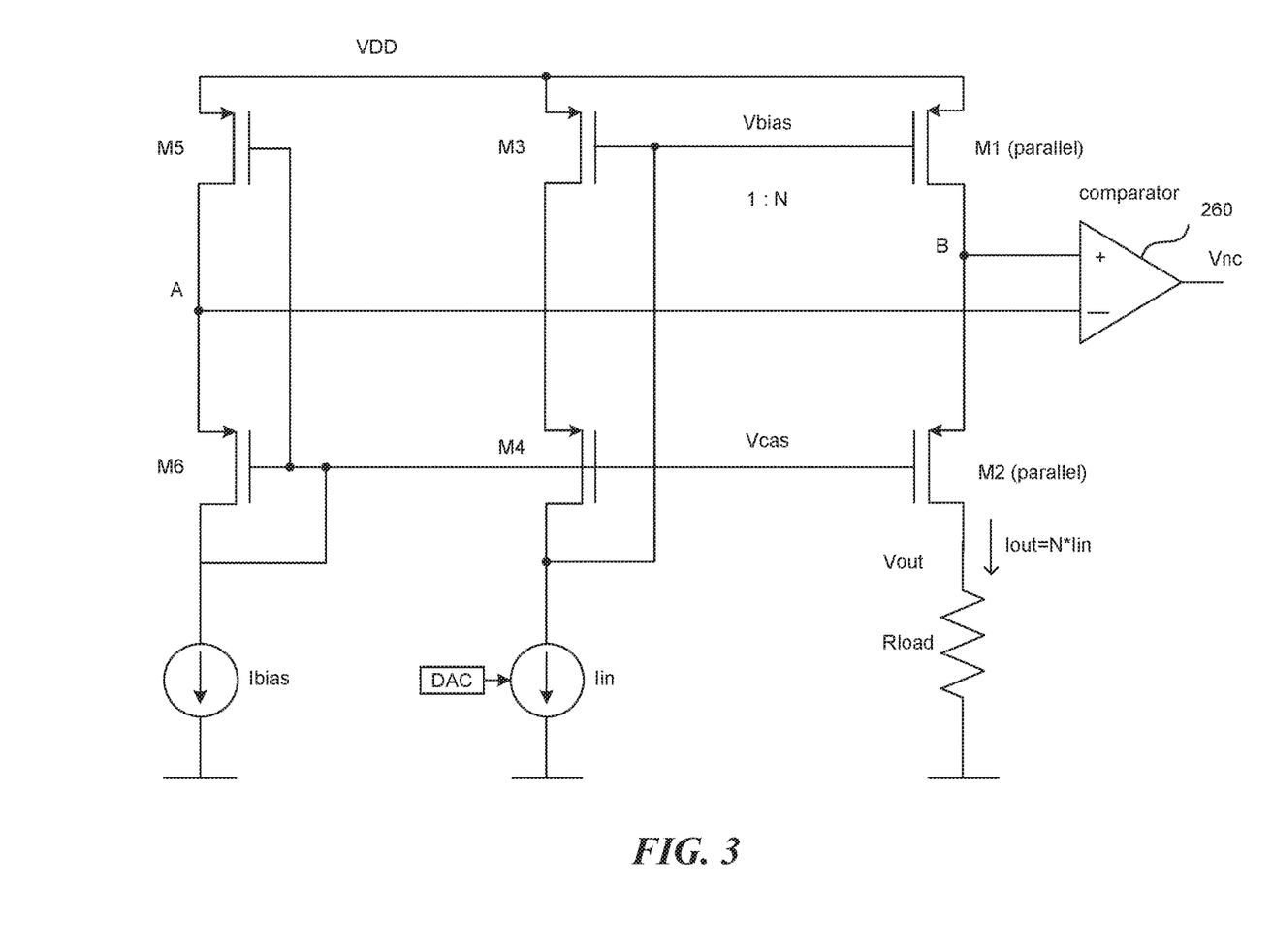
FIG. 3 is a circuit diagram of a therapeutic current-generating circuit that includes a voltage monitoring circuit in accordance with a disclosed embodiment of the present technology.

FIG. 3 shows one embodiment of the current-generating circuit 202 that includes a voltage monitoring circuit and is configured to manage the competing requirements described above. The current-generating circuit 202 includes a current mirror circuit. The current mirror circuit includes a control portion and a controlled portion including a number of MOSFET or other transistors labelled M1, M2, M3 and M4. Each of the transistors M1 and M2 is actually a number of MOSFET transistors that are connected in parallel although only one transistor is shown for ease of illustration. In the embodiment shown, the controlled portion of the current mirror includes a first number of parallel-connected MOSFET transistors M1 that are in series with a second number of parallel-connected MOSFET transistors M2. The first number of parallel-connected transistors M1 have their source terminals connected to the supply voltage $V_{DD}$ and their drain terminals connected to the source terminals of the second number of parallel-connected transistors M2. The drain terminals of second number of parallel-connected transistors M2 are connected to the load (e.g., the electrodes or contacts on the leads).

The control portion of the current mirror includes a third MOSFET transistor M3 and a fourth MOSFET transistor M4 that are connected in series between a supply voltage $V_{DD}$ and a programmable current source $I_{in}$. In the embodiment shown, the source terminal of the third transistor M3 is connected to $V_{DD}$ and the drain terminal is connected to a source terminal of the fourth transistor M4. The gate electrodes of transistors M1 and M3 are connected together and are tied to the drain terminal of transistor M4. The drain terminal of the fourth transistor M4 is connected to the programmable current source $I_{in}$.

Because the transistors in the current mirror are matched and because the third transistor M3 and the first number of parallel-connected transistors M1 are commonly biased, the current flowing though the controlled half of the current mirror (parallel sets of transistors M1 and M2) will be N times the current set by the programmable current source $I_{in}$, where N is the number of transistors connected in parallel. In one embodiment, N is equal to 100 so the current delivered to the load is 100 times the programmable current $I_{in}$. In one embodiment, the programmable current $I_{in}$ is controlled by a digital-to-analog converter (DAC) to produce a current between 0 and 150 microamps. The current delivered to the load is therefore controllable between 0 and 15 milliamps. Although the disclosed current mirror uses P-channel MOSFETS, it will be appreciated that other suitable transistors can be used to implement the current mirror. The details of a current mirror circuit are considered well known to persons of ordinary skill in the art of electronics and are therefore not discussed in further detail.

To determine if the voltage level supplied by the programmable voltage regulator 208 is sufficient to allow the current mirror to deliver the requested current, a current source supply voltage monitoring circuit is included in the current-generating circuit 202. The supply voltage monitoring circuit includes a comparator 260 having inputs that compare the voltage at two nodes labelled "A" and "B." The voltage at node A is taken at a point in a reference current path that is formed by fifth and sixth MOSFET transistors M5 and M6. The fifth and sixth transistors M5 and M6 in the reference current path are connected in series between the supply voltage $V_{DD}$ and a constant current source $I_{bias}$. The source terminal of the fifth transistor M5 is connected to the supply voltage $V_{DD}$ and the drain terminal of transistor M5 is connected to a source terminal of the sixth transistor M6. The drain terminal of the sixth transistor M6 is connected to the constant current source $I_{bias}$. In one embodiment, the constant current source $I_{bias}$ is implemented with a band gap circuit and a precision resistor. The gates of the fifth and sixth transistors M5 and M6 are tied to the constant current source $I_{bias}$. The gates of transistors M2 and M4 in the current mirror are also tied to the constant current source $I_{bias}$ so that the gates of transistors M6, M4 and the second set of parallel-connected transistors M2 in the current mirror are commonly biased. In one embodiment, the current $I_{bias}$ is set so the transistor M6 remains in saturation regardless of the level of $V_{DD}$ or the level of the requested current while transistor M5 will usually be in the linear (or triode) region.

To monitor the voltage $V_{DD}$ that is supplied to the current-generating circuit 202, the comparator 260 compares the voltage at node A (between the drain terminal of the fifth transistor M5 and the source terminal of the sixth transistor M6 in the reference current path) with the voltage at node B (between the drain terminals of the first set of parallel-connected transistors M1 and the source terminals of the second set of parallel-connected transistors M2). When the voltage at node A is larger than the voltage at node B, the output of the comparator 260 is negative or –zero. Conversely, when the voltage at node B exceeds the voltage at node A, the output of the comparator 260 is positive. The comparator 260 may be a separate integrated circuit or if the comparator 260 is to be integrated with other circuitry of the system, the comparator may be made of discrete components including a differential pair of transistors. The details of designing a comparator are considered well known to those of ordinary skill in the art of circuit design.

The voltage at node A tracks the supply voltage $V_{DD}$. Accordingly, as the voltage $V_{DD}$ increases, the voltage at node A increases. Similarly, as the supply voltage $V_{DD}$ decreases, the voltage at node A also decreases. When the supply voltage is set high enough so that the first and second sets of parallel-connected transistors M1 and M2 can supply the requested current to the load, the transistors will be operating in the saturation region. However, if the supply voltage is decreased to the point that the transistors can no longer supply the requested current, the parallel-connected transistors M2 and/or M1 will come out of saturation and the voltage at node B increases with respect to the voltage at node A. When the difference between $V_{DD}$ and the voltage at node B becomes less than the difference between $V_{DD}$ and the voltage at node A, the comparator 260 produces an output signal $V_{NC}$ (voltage non-compliant) that indicates that the supply voltage $V_{DD}$ is insufficient to allow the current mirror to produce the requested current.

Figure 4:
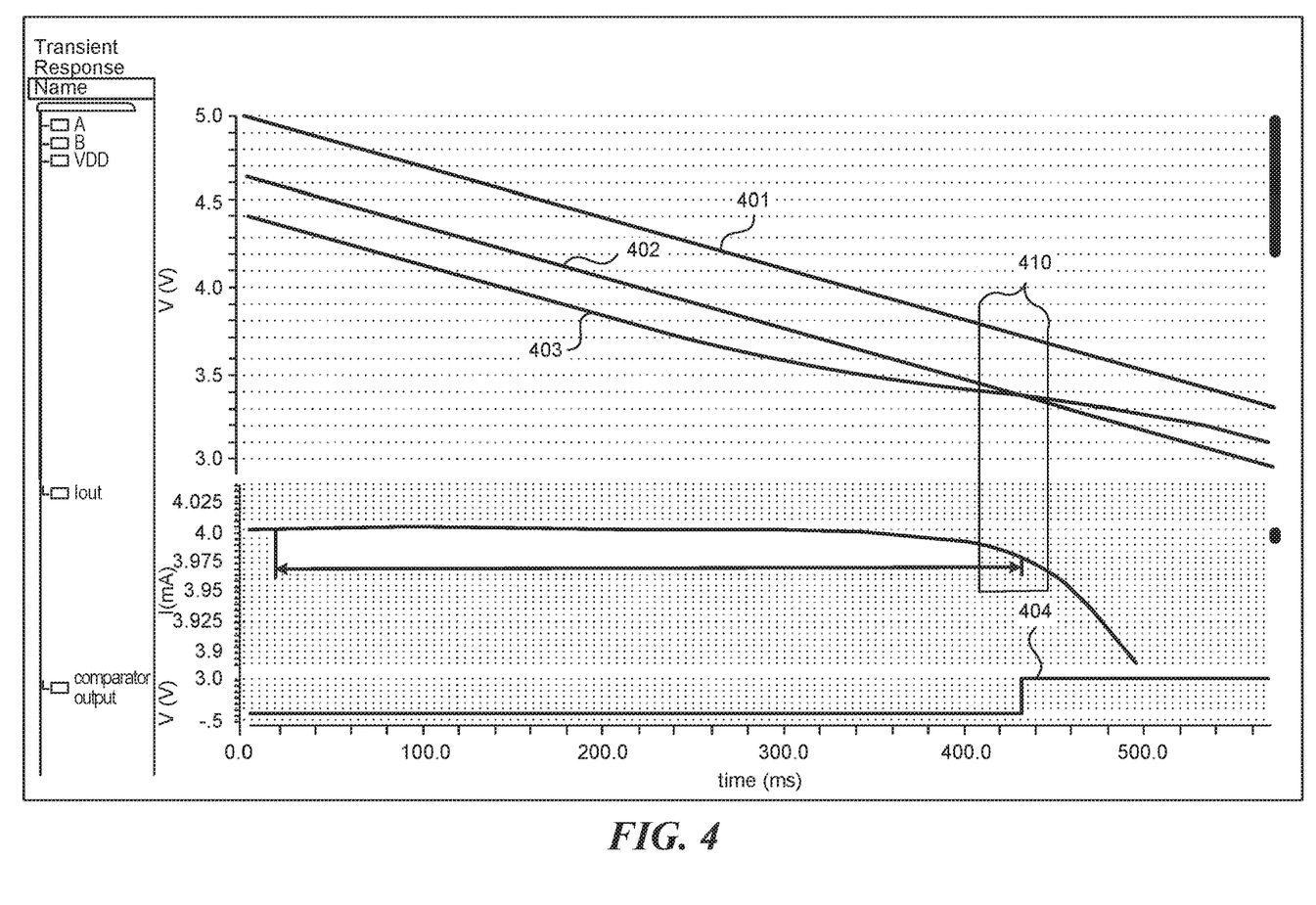
FIG. 4 is a simulation of the operation of the voltage monitoring circuit shown in FIG. 3.

In one embodiment, the output $V_{NC}$ of the comparator 260 is fed to the processor 210, which is programmed to interpret the $V_{NC}$ signal. In one embodiment, the processor 210 is programmed to instruct the programmable voltage regulator 208 to increase the supply voltage to a point where the comparator output, $V_{NC}$, once again becomes negative after detecting a positive $V_{NC}$ signal. On the other hand, if the signal $V_{NC}$ is negative, the processor can instruct the programmable voltage regulator 208 to reduce the supplied voltage and save battery power FIG. 4 shows a plot of voltages in the current-generating circuit 202 versus changes in the supplied voltage $V_{DD}$. A first line 401 represents the supply voltage $V_{DD}$ as it is decreased. A second line 402 represents the voltage at node A in FIG. 3 and a third line 403 represents the voltage at node B in FIG. 3. As shown, the voltage at node A varies with changes in the supply voltage. The voltage at node A tracks (e.g., remains a constant difference with respect to) variations in the supply voltage $V_{DD}$. The voltage at node B tracks the supply voltage until the point 410 (circled) when the transistors of the current mirror can no longer supply the requested current. At this point, the voltage across the transistors in the controlled portion of the current mirror decrease and the voltage at node B becomes larger than the voltage at node A. Accordingly, the output of the comparator (indicated by line 404) changes states. The comparator 260 can be very sensitive and in one embodiment, can change states when the current difference is less than 0.5-0.9% from the requested current.

Figure 5:
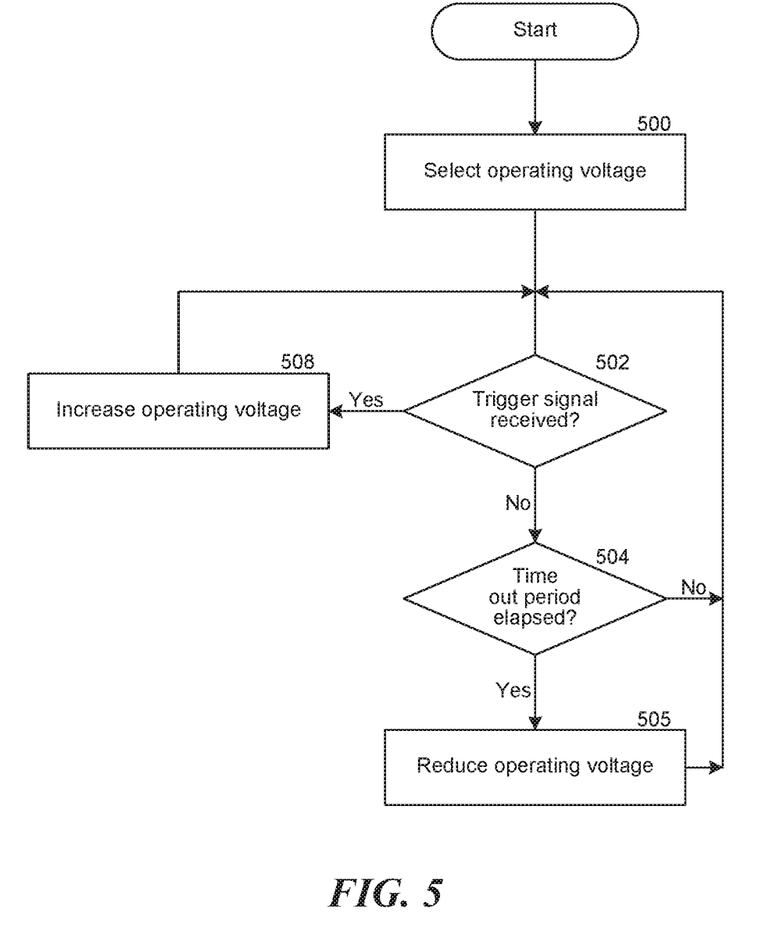
FIG. 5 is a flow chart of steps performed by a logic device in an implantable therapeutic device in accordance with a disclosed embodiment of the present technology.

FIG. 5 is a flow diagram of steps performed by a programmed processor to monitor and adjust the voltage supplied from a battery to a current-generating circuit in accordance with particular disclosed embodiments. Beginning at block 500, the processor controls the programmable voltage regulator 208 to provide an initial operating voltage. Such a voltage may be the highest operating voltage that the voltage regulator is able to produce from the battery or may be a lessor voltage that is selected according to a previously determined mapping of a supply voltage versus a requested current to be delivered to the electrodes. Such a mapping can be based on circuit testing as the current-generating circuit 202 is being designed or tested.

At block 502, the processor determines if the trigger signal $V_{NC}$ from the comparator indicates that the supply voltage is non-compliant for the requested current to be delivered. In one embodiment, the processor can periodically poll an input port that is connected directly or indirectly to the output of the comparator. In another embodiment, the output of the comparator can be connected directly or indirectly to an interrupt port that triggers the processor to perform a desired sequence of actions when the comparator changes states.

If the answer at block 502 is yes and the comparator indicates that the supply voltage is non-compliant, then the processor instructs the programmable voltage regulator 208 to increase the supply voltage $V_{DD}$ at block 508. For example, the processor may execute instructions that direct the programmable voltage regulator to supply a desired voltage to (e.g. supply 6.3 Volts). Alternatively, the processor may execute instructions that cause the processor to produce a signal (digital or analog) that is detected by the programmable voltage to increase or decrease the supplied voltage. Other instructions are also possible that, for example, cause the processor to instruct the programmable voltage supply to increase or decrease the supplied voltage by a determined amount (e.g. +2.3 Volts, −1.6 Volts). In one embodiment, this process continues until such time as the comparator changes states to indicate that the supply voltage is compliant.

If the answer at block 502 is no, the processor determines if a time-out period has elapsed at block 504. In one embodiment, the time out period is set to prevent the processor from changing the supply voltage too rapidly. If the time-out period has not elapsed, processing returns to block 502 to check for the trigger signal.

If the time-out period has elapsed at block 504, then the processor instructs the programmable voltage regulator 208 to lower or reduce the supply voltage $V_{DD}$ at block 506. In this manner the supply voltage is kept at a level that is just above the level needed by the current-generating circuit to supply the requested current to the load.

As will be appreciated, other embodiments of the presently disclosed technology can include other algorithms for adjusting the supply voltage. For example, once a non-compliant supply voltage is detected or determined, the supply voltage can be increased and then not changed until a new trigger signal is received. In yet another embodiment, the processor can be programmed to increase or decrease the supply voltage by non-uniform steps in order to quickly determine the voltage level at which the supply voltage is compliant.

Embodiments of the subject matter and the operations described herein can be implemented in digital electronic circuitry, or in computer software, firmware, or hardware, including the structures disclosed herein and their structural equivalents, or in combinations of one or more of them. Embodiments of the subject matter described in this specification can be implemented as one or more computer programs, i.e., one or more modules of computer program instructions, encoded on or in computer storage media for execution by, or to control the operation of, a data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium also can be, or can be included in, one or more separate physical components or media (e.g., RAM, ROM, EPROM, EEPROM, or other storage devices). The operations described in this specification can be implemented as operations performed by a data processing apparatus on data stored on one or more computer-readable storage devices or received from other sources.

The term "processor" encompasses a wide variety of suitable of apparatus, devices, and machines for processing data, including for example, a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). Logic circuitry as used herein therefore includes both special purpose logic circuitry and general purpose logic circuitry like a programmed processor.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code).

The processes and logic flows described herein can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special-purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data.

In another embodiment, the processor that receives the signal from the voltage monitoring circuit is replaced with an FPGA, ASIC or other dedicated logic circuit that implements a control algorithm to control the programmable voltage regulator in response to the signal from the voltage monitoring circuit.

3.0 Additional Embodiments

In one embodiment, the system includes an implantable control unit having a rechargeable battery and a processor. The control unit further includes one or more current-generating circuits that use a current mirror to deliver a requested current to one or more electrodes. A voltage monitoring circuit includes a detector that detects when a supply voltage is not sufficient to allow the current mirror to produce the requested current.

In some embodiments, the voltage monitoring circuit includes a comparator that compares the voltage at two reference nodes in the current-generating circuit. The first reference node produces a voltage that tracks changes in the supply voltage while the second reference node produces a voltage that tracks changes in the supply voltage until a point where the current delivered to the electrodes differs from a requested current. At this point, the comparator produces an output signal that indicates that the supply voltage is insufficient to allow the current mirror to produce the requested current.

In one embodiment, a processor is configured to receive the output signal of the comparator and to adjust the supply voltage produced from the battery to a level that is sufficient to allow the current-generating circuit to produce the requested current but not so great that excess power from the battery is wasted.

From the foregoing, it will be appreciated that specific embodiments of the disclosed technology have been described herein for purposes of illustration, but that various modifications may be made without deviating from the technology. Certain aspects of the technology described in the context of particular embodiments may be combined or eliminated in other embodiments. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A voltage monitoring circuit for use with a system that delivers therapeutic pulses to a patient of the type that includes:
    a voltage regulator coupleable to a battery and that is configured to produce a variable supply voltage;
    a current-generating circuit configured to supply a requested current to one or more electrodes more transistors coupled to the variable supply voltage and configured to be in saturation when supplying the requested current, the voltage monitoring circuit comprising:
    a reference current path that includes a transistor coupled to the variable supply voltage that is configured to produce a voltage at a terminal that tracks the variable supply voltage; and
    a comparator circuit configured to produce a signal when the supply voltage produced by the voltage regulator is insufficient to allow the current-generating circuit to supply the requested current, wherein the comparator circuit has a first input coupled to the terminal of the transistor in the reference current path to sense the voltage that tracks the variable supply voltage, and a second input coupled to a terminal of the one or more transistors in the current-generating circuit to sense a voltage drop across the one or more transistors in the current-generating circuit, and wherein the comparator is configured to produce the signal that indicates the variable supply voltage produced by the voltage regulator is sufficient to allow the current-generating circuit to supply the requested current when the voltage at the second input exceeds the voltage at the first input.

2. The voltage monitoring circuit of claim 1, wherein the first input is taken at a node that is located between the transistor in the reference current path and a constant current source.

3. The voltage monitoring circuit of claim 2, wherein the current-generating circuit includes sets of parallelly connected transistors are wherein the second input is taken at a node that is located between the sets of parallelly connected transistors that supply the requested current.

4. The voltage monitoring circuit of claim 1, wherein the transistor coupled to the variable supply voltage in the reference current path is biased to operate in a linear region.

5. A circuit configured to monitor if a supply voltage is insufficient to allow a current-generating circuit to cupply a requested current, comprising:
    a battery;
    a processor;
    a programmable voltage regulator coupled to the battery and configured to produce a variable supply voltage;
    a supply voltage monitoring circuit configured to produce a signal that is indicative of whether the variable supply voltage produced by the programmable voltage regulator is in sufficient to allow a current-generating circuit including one or more transistors coupled to the variable supply voltage to supply the requested current, wherein the supply voltage monitoring circuit includess:
        a reference current path that includes a transistor coupled to the variable supply voltage that is configured to produce a voltage at a terminal that tracks the variable supply voltage; and
    a comparator circuit having a first input coupled to the terminal of the transistor in the reference current path to sense the voltage that tracks the variable supply voltage and a second input coupled to a terminal of the one or more transistors in the current-generating circuit to sense a voltage drop across the one or more transistors in the current-generating circuit wherein the comparator is configured to produce the signal that indicates that the variable supply voltage produced by the programmable voltage regulator is insufficient to allow the current-generating circuit to supply the requested current when the voltage at the second input exceeds the voltage at the first input; and
    wherein the processor is configured to receive the signal from the supply voltage monitoring circuit and is configured to execute instructions to control the programmable voltage regulator to change the variable supply voltage provided to the current-generating circuit.

6. The circuit of claim 5, wherein the processor is configured to execute instructions that cause the processor to control the programmable voltage regulator to decrease the variable supply voltage if the signal from the supply voltage monitoring circuit indicates that the variable supply voltage is sufficient to allow the current-generating circuit to produce the requested current.

7. The circuit of claim 6, wherein the processor is configured to execute instructions that cause the processor to wait a period of time after the processor detects the signal from the supply voltage monitoring circuit before controlling the programmable voltage regulator.

8. The circuit of claim 5, wherein the processor is configured to execute instructions that cause the processor to control the programmable voltage regulator to increase the variable supply voltage if the signal from the supply voltage monitoring circuit indicates that the variable supply voltage is insufficient to allow the current-generating circuit to produce the requested current.

9. The circuit of claim 5, wherein the transistor coupled to the variable supply voltage in the reference current path is biased to operate in a linear region.

* * * * *